United States Patent
Kouno et al.

(10) Patent No.: US 10,455,201 B2
(45) Date of Patent: Oct. 22, 2019

(54) IMAGING DEVICE, MANUFACTURING METHOD THEREOF, AND MEDICAL IMAGING SYSTEM

(71) Applicant: SONY CORPORATION, Tokyo (JP)

(72) Inventors: Rui Kouno, Kanagawa (JP); Tadamasa Kurashige, Kanagawa (JP); Takuma Tanae, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 95 days.

(21) Appl. No.: 15/540,175

(22) PCT Filed: Mar. 1, 2016

(86) PCT No.: PCT/JP2016/001099
§ 371 (c)(1),
(2) Date: Jun. 27, 2017

(87) PCT Pub. No.: WO2016/152036
PCT Pub. Date: Sep. 29, 2016

(65) Prior Publication Data
US 2018/0013989 A1    Jan. 11, 2018

(30) Foreign Application Priority Data
Mar. 24, 2015   (JP) .................... 2015-060659

(51) Int. Cl.
| H04N 17/00 | (2006.01) |
| H04N 17/02 | (2006.01) |
| H04N 9/093 | (2006.01) |
| G06T 7/80 | (2017.01) |
| G06T 7/30 | (2017.01) |
| A61B 1/00 | (2006.01) |
| A61B 1/04 | (2006.01) |

(Continued)

(52) U.S. Cl.
CPC .......... *H04N 9/093* (2013.01); *A61B 1/0011* (2013.01); *A61B 1/04* (2013.01); *A61B 1/0638* (2013.01);
(Continued)

(58) Field of Classification Search
CPC ............. H04N 9/093; H04N 9/097; H04N 2005/2255; A61B 1/0011; A61B 1/04;
(Continued)

(56) References Cited

U.S. PATENT DOCUMENTS

| 5,453,840 A | 9/1995 | Parker et al. |
| 2001/0030697 A1 | 10/2001 | Dischert et al. |

(Continued)

FOREIGN PATENT DOCUMENTS

| EP | 0 518 185 A2 | 12/1992 |
| JP | S55-091275 A | 7/1980 |

(Continued)

OTHER PUBLICATIONS

"Sony Global—IMX226CQJ,", 2014, XP055268911, 3 pages.
International Search Report dated May 6, 2016 in PCT/JP2016/001099 filed Mar. 1, 2016.

*Primary Examiner* — Kelly L Jerabek
(74) *Attorney, Agent, or Firm* — Oblon, McClelland, Maier & Neustadt, L.L.P.

(57) ABSTRACT

An imaging device includes a light separator that separates light into light bands, and imaging elements that each receives one of the light bands and generates a corresponding signal. Each of the imaging elements has a pixel size of at most 2.5 μm by 2.5 μm. A registration error among the imaging elements is equal to or less than a threshold determined according to the pixel size.

12 Claims, 9 Drawing Sheets

(51) Int. Cl.
*A61B 1/06* (2006.01)
*H04N 5/225* (2006.01)

(52) U.S. Cl.
CPC ............... *G06T 7/30* (2017.01); *G06T 7/80* (2017.01); *H04N 5/2256* (2013.01); *H04N 17/002* (2013.01); *G06T 2207/10024* (2013.01); *G06T 2207/10068* (2013.01); *H04N 2005/2255* (2013.01)

(58) Field of Classification Search
CPC .. A61B 1/041; G06T 7/80; G06T 7/85; G06T 2207/10068
USPC ............................................ 348/45, 65, 187
See application file for complete search history.

(56) References Cited

U.S. PATENT DOCUMENTS

| | | | | |
|---|---|---|---|---|
| 2002/0113885 | A1* | 8/2002 | Inoue | H04N 5/217 348/280 |
| 2002/0114536 | A1* | 8/2002 | Xiong | G06K 9/32 382/284 |
| 2005/0083531 | A1* | 4/2005 | Millerd | G01J 3/2803 356/450 |
| 2006/0125842 | A1* | 6/2006 | Kim | G06T 3/4015 345/611 |
| 2008/0037906 | A1* | 2/2008 | Yano | H04N 9/045 382/312 |
| 2009/0021598 | A1* | 1/2009 | McLean | G01J 3/02 348/222.1 |
| 2010/0149183 | A1* | 6/2010 | Loewke | G06K 9/00134 345/424 |
| 2011/0025905 | A1 | 2/2011 | Tanaka | |
| 2015/0124114 | A1* | 5/2015 | Kamiya | G06T 3/4015 348/222.1 |

FOREIGN PATENT DOCUMENTS

| | | |
|---|---|---|
| JP | S57-143769 U | 9/1982 |
| JP | H07-046613 A | 2/1995 |
| JP | 2008-103845 A | 5/2008 |
| JP | 2011-235109 A | 11/2011 |

* cited by examiner

[Fig. 1]
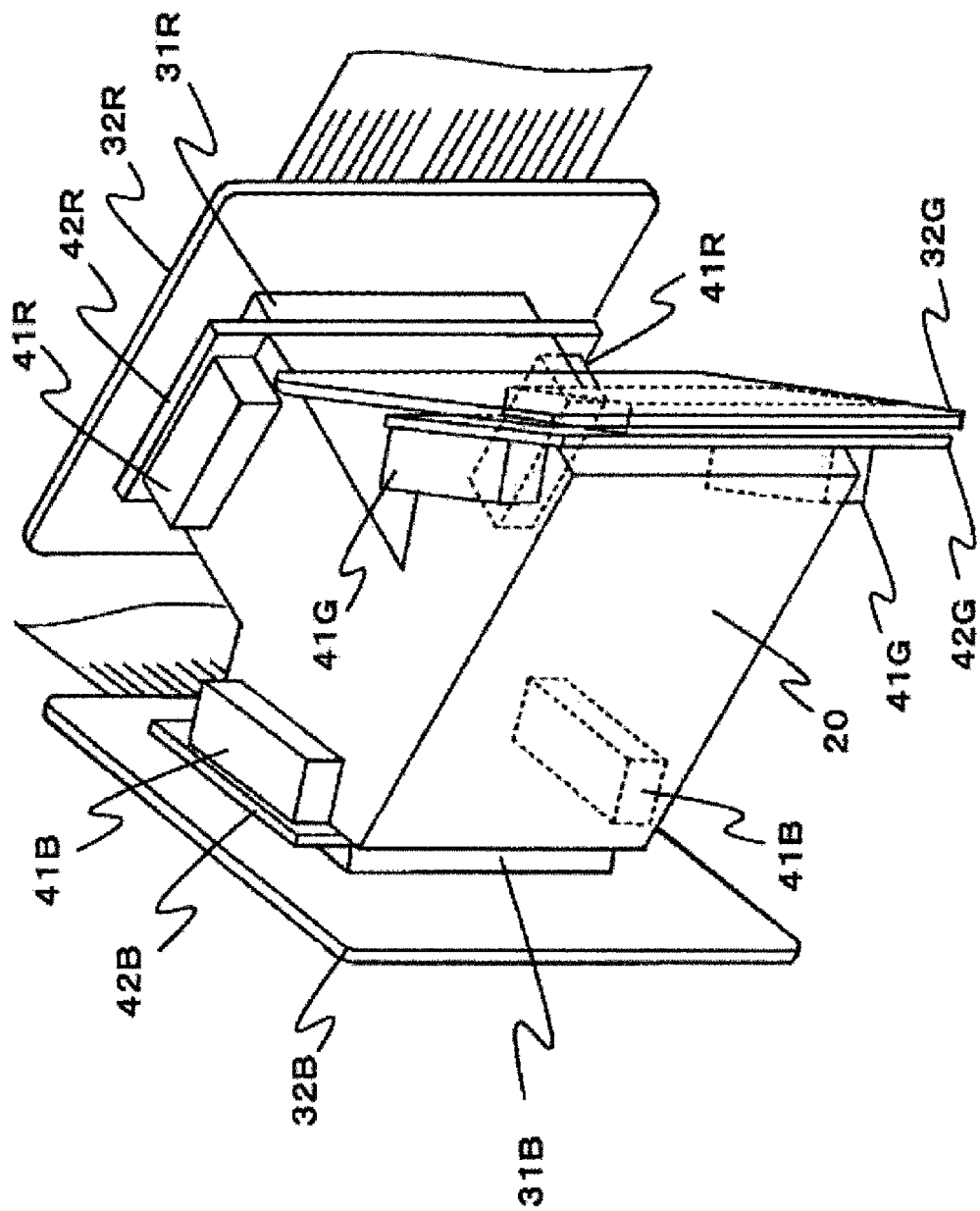

[Fig. 2]
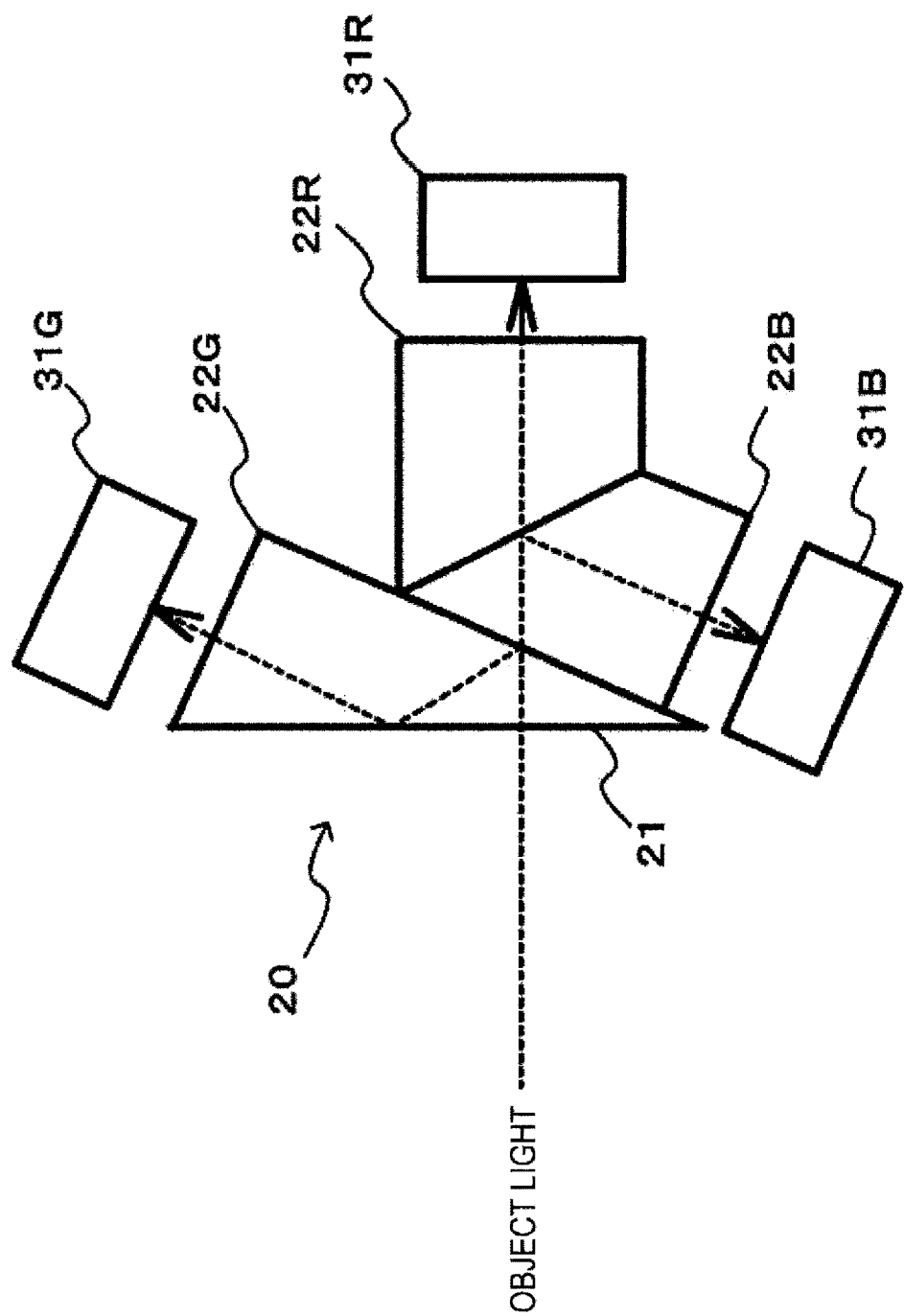

[Fig. 3]
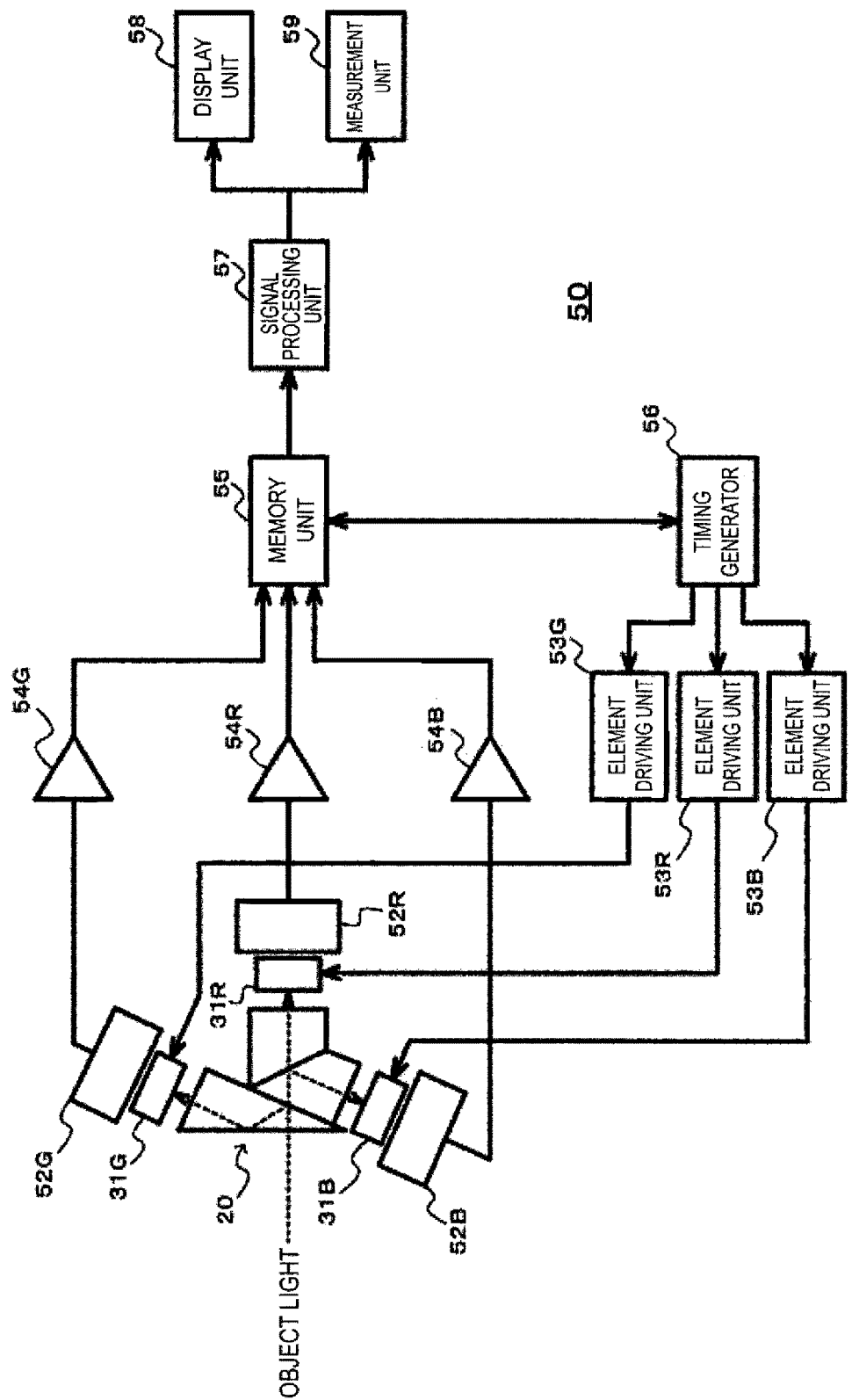

[Fig. 4]
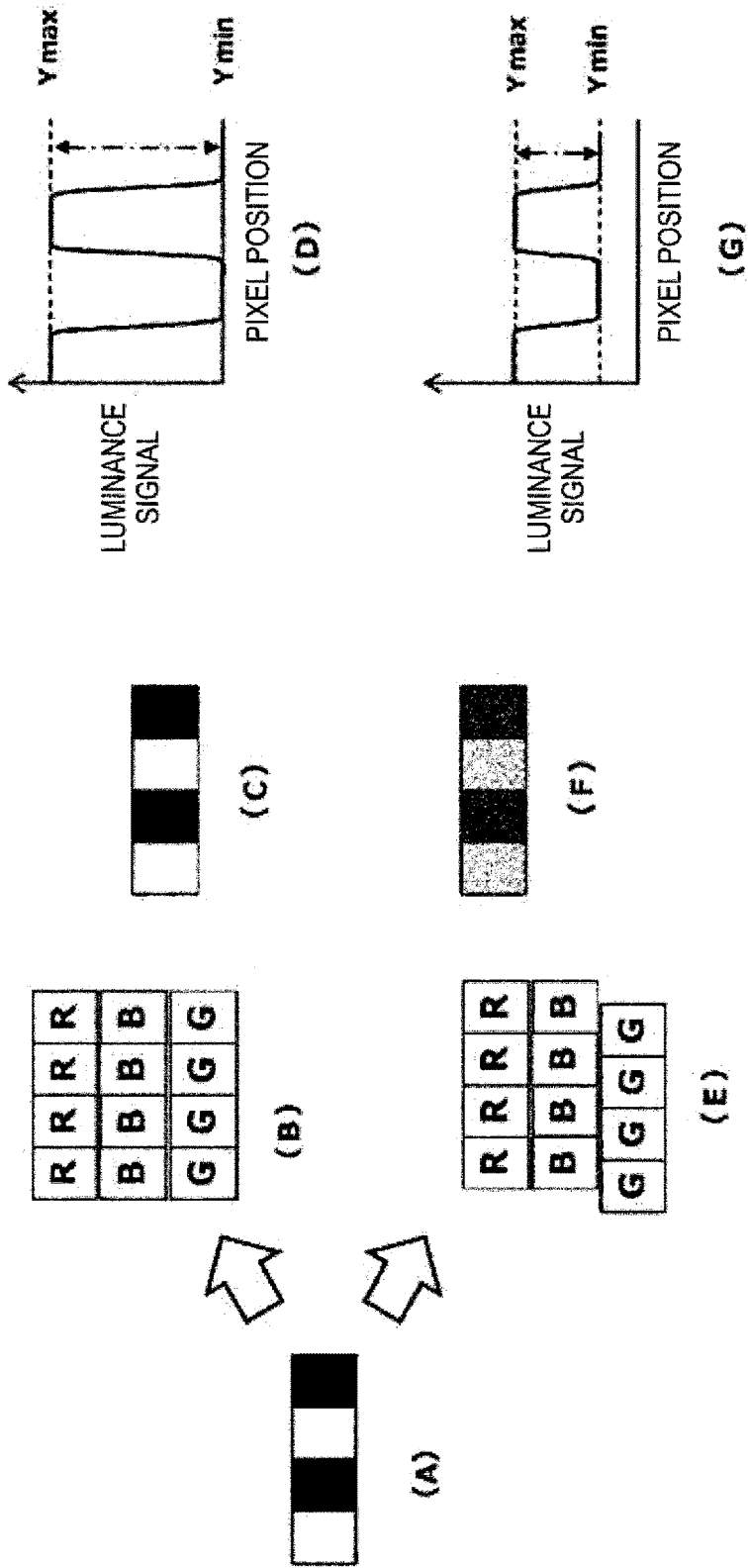

[Fig. 5]
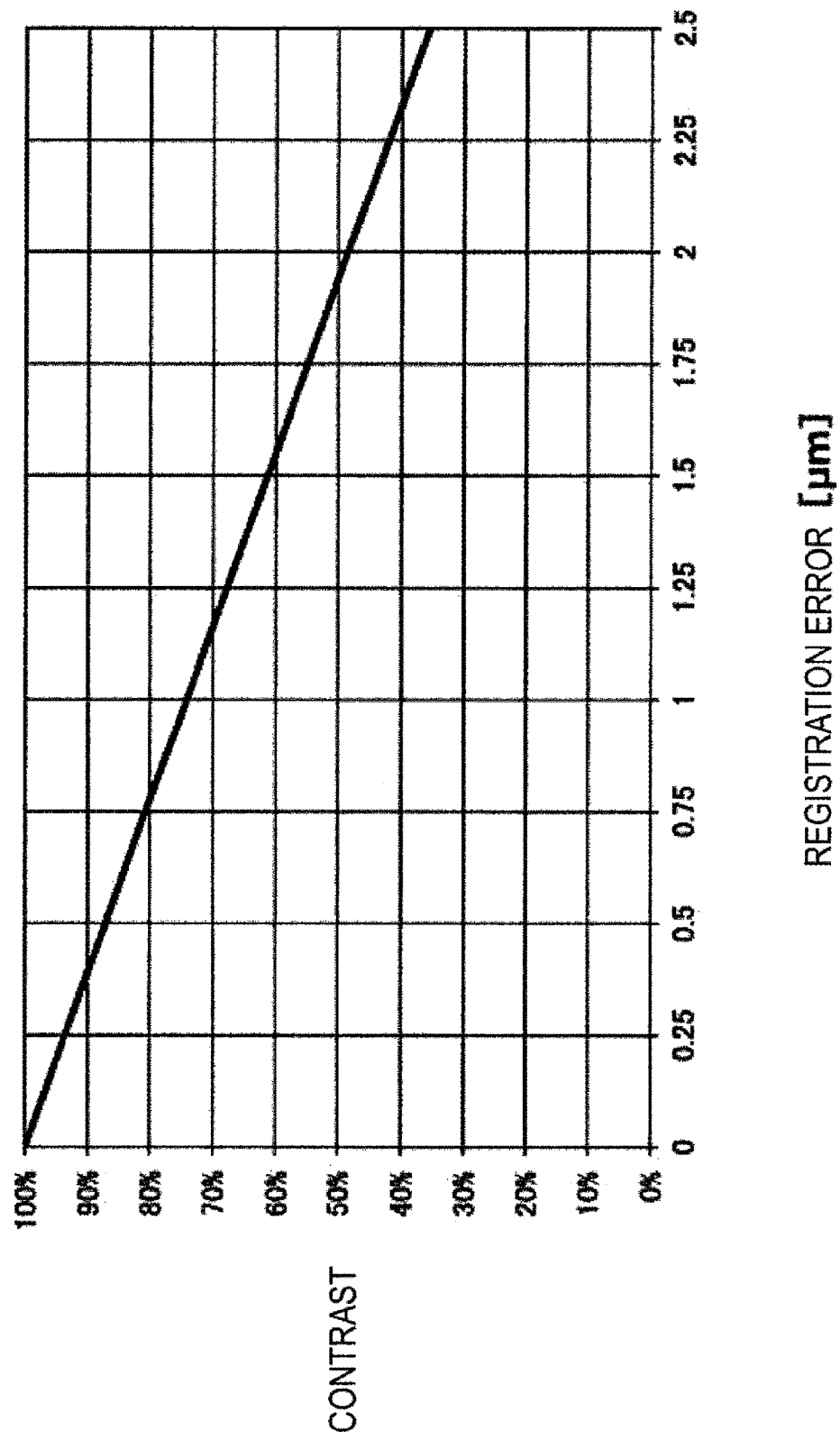

[Fig. 6]
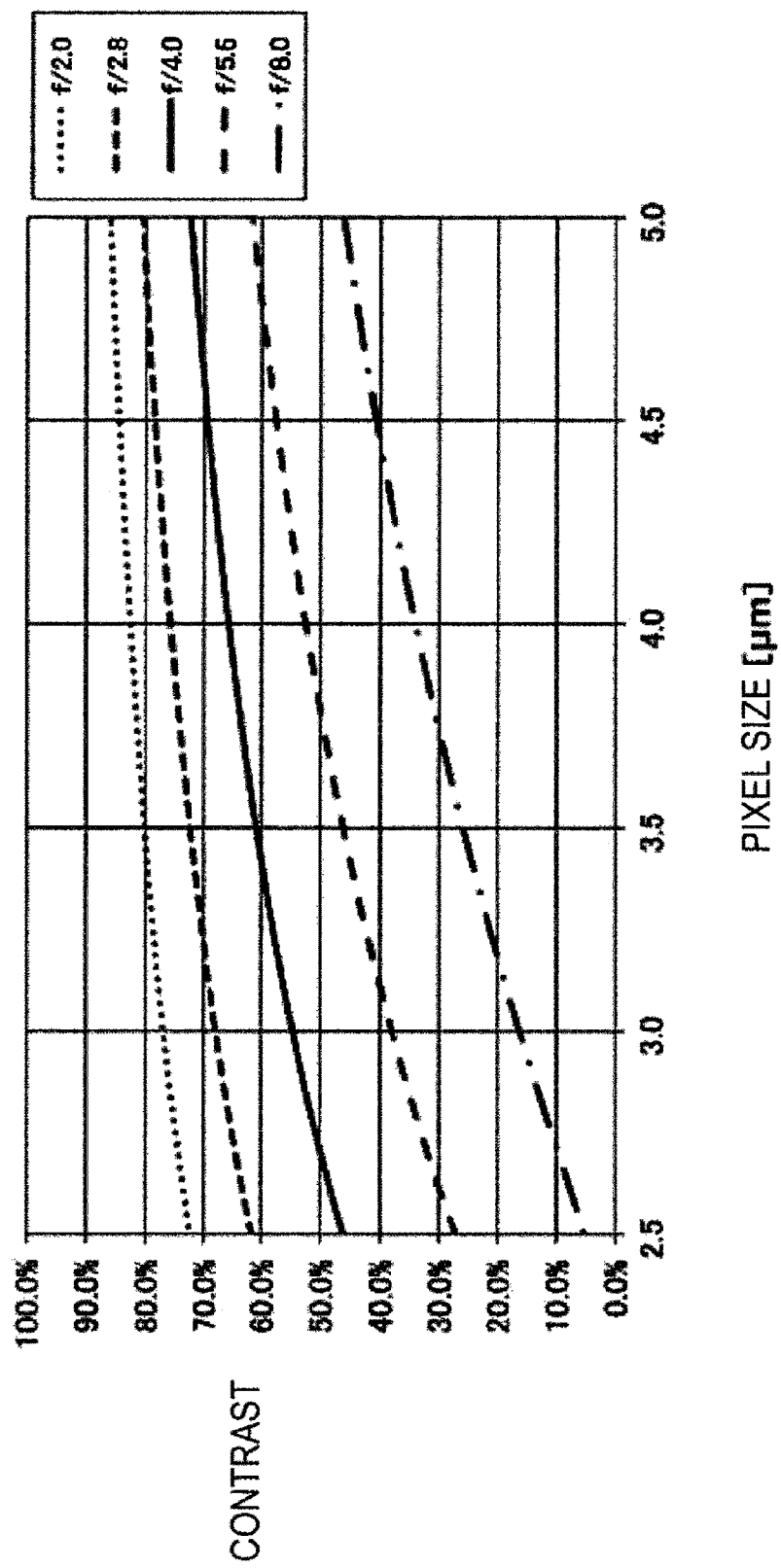

[Fig. 7]
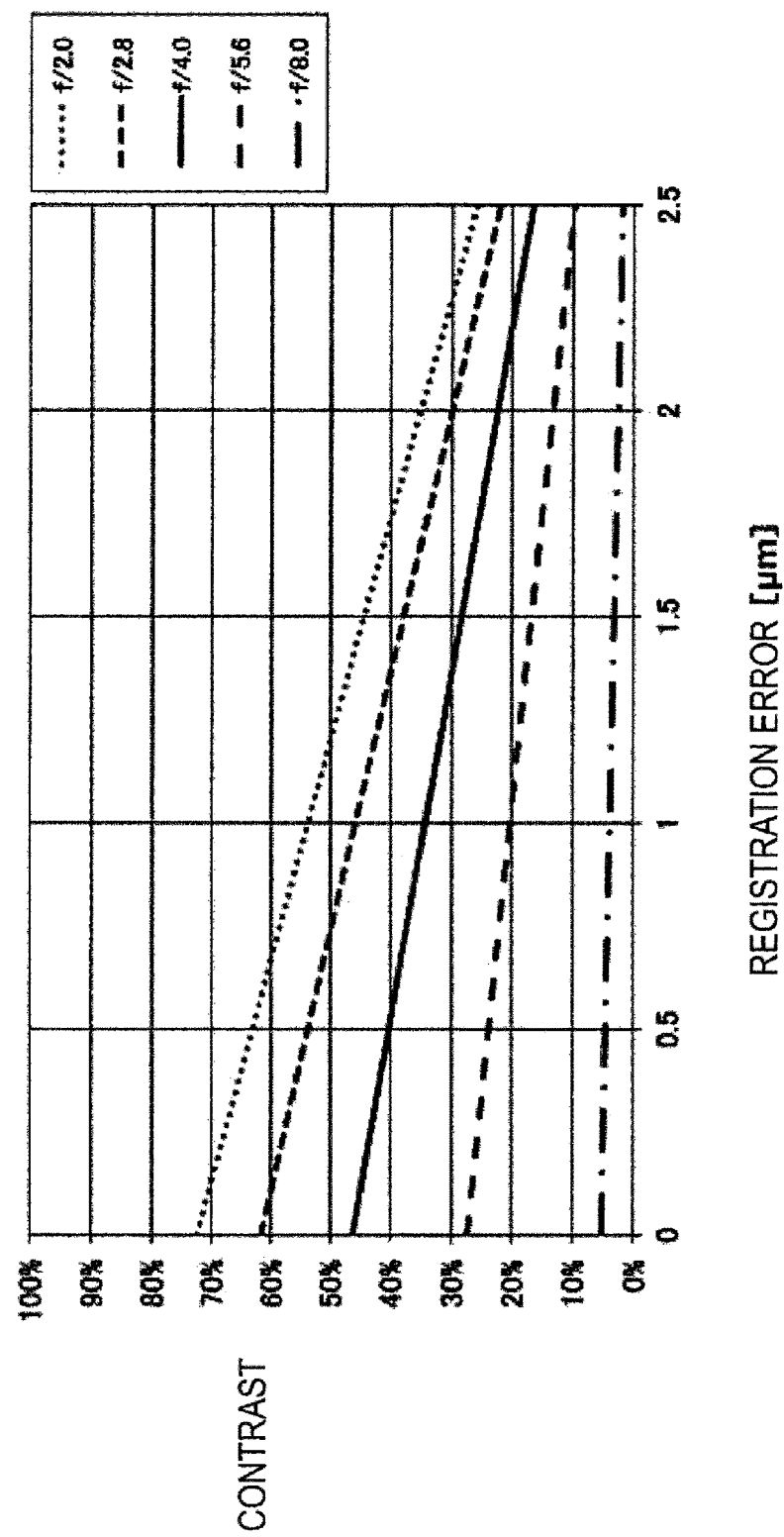

[Fig. 8]
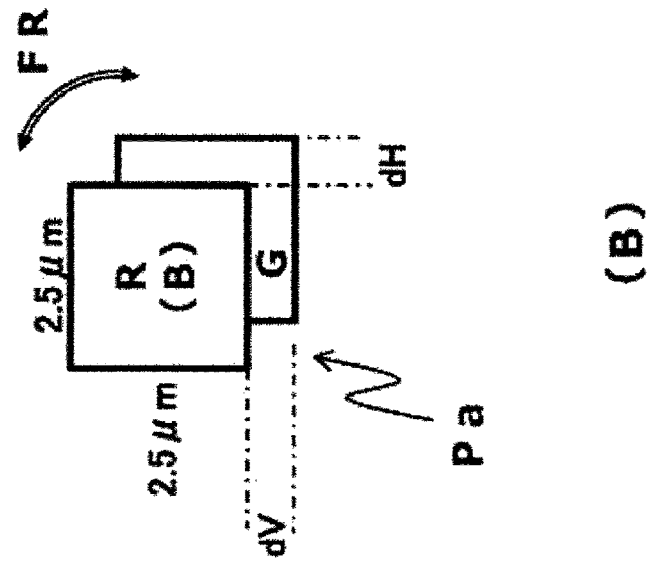
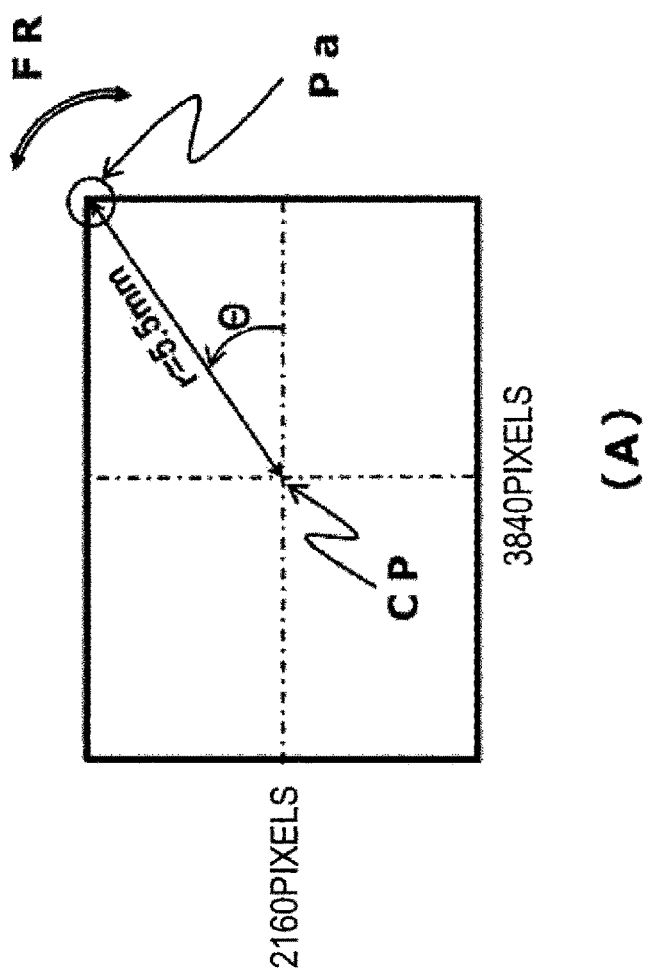

[Fig. 9]
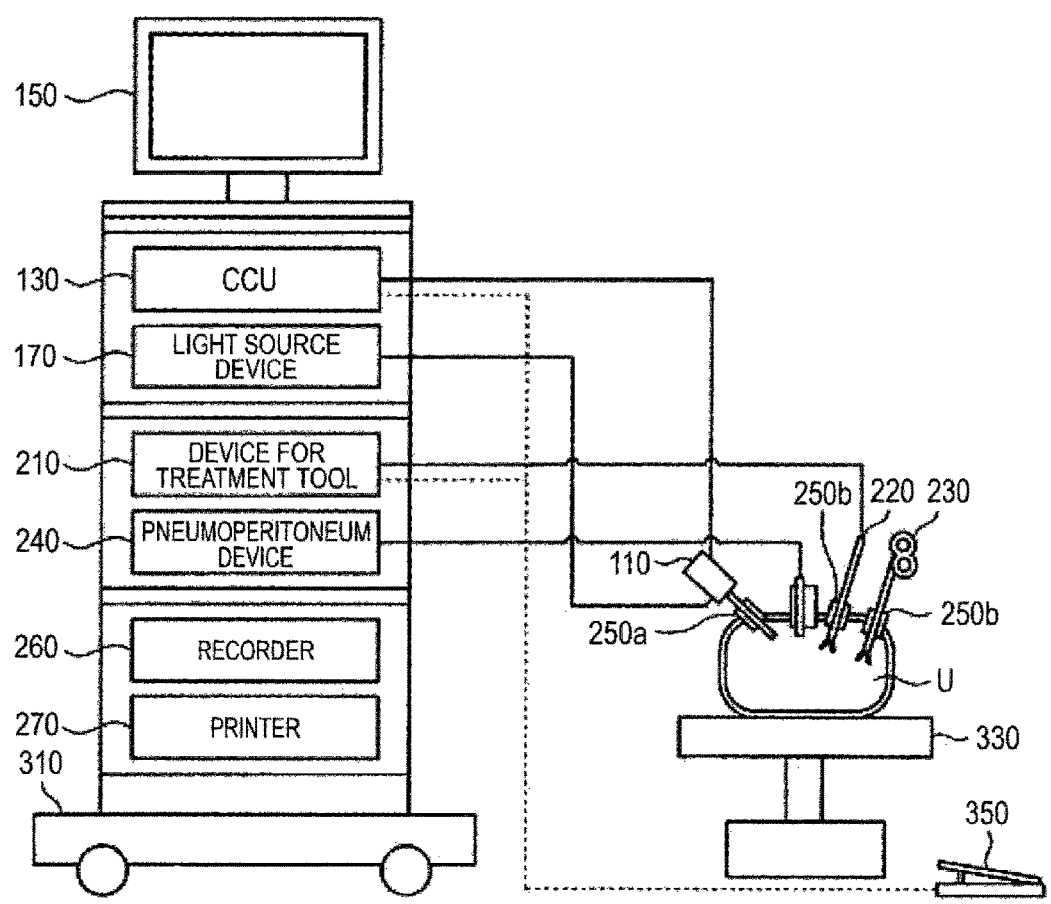

IMAGING DEVICE, MANUFACTURING METHOD THEREOF, AND MEDICAL IMAGING SYSTEM

CROSS REFERENCE TO RELATED APPLICATIONS

This application claims the benefit of Japanese Priority Patent Application JP 2015-060659 filed Mar. 24, 2015, the entire contents of which are incorporated herein by reference.

TECHNICAL FIELD

This technology relates to an imaging device, a manufacturing method thereof and a medical imaging system.

BACKGROUND ART

Solid-state imaging devices provided with three imaging elements for red, green, and blue have been known in related art. In such an imaging device, as disclosed in PTL 1, imaging light is separated into imaging light of three primary colors by a color separation prism of an imaging optical system. The imaging light of each color enters the imaging element for the corresponding color to be subjected to photoelectric conversion; thus, an imaging signal is generated and output for each color.

CITATION LIST

Patent Literature

PTL 1: JP 2008-103846A

SUMMARY

Technical Problem

Imaging devices have been undergoing increases in the resolution of imaging elements so as to be able to provide captured images with high definition and high image quality. Meanwhile, the size of imaging elements is set equal to the size in related art so that lenses that have been numerously provided can be applied. Therefore, the pixel size of individual imaging elements is reduced as compared with that in related art, which makes contrast degradation or the like due to misregistration more significant and makes it difficult to acquire captured images with high image quality. In addition, manufacturing imaging devices such that there is no misregistration results in lowered productivity and increased manufacturing cost.

Thus, it is desirable to provide an imaging device that can acquire captured images with high definition and high image quality easily and inexpensively.

Solution to Problem

In one exemplary aspect, an imaging device includes a light separator that separates light into a plurality of light bands, and a plurality of imaging elements that each receives one of the plurality of light bands and generates a corresponding signal. Each of the imaging elements has a pixel size of at most 2.5 μm by 2.5 μm. A registration error among the plurality of imaging elements is equal to or less than a threshold determined according to the pixel size.

In another exemplary aspect, a method of manufacturing an imaging device includes providing a light separator on a fixing device and providing a plurality of imaging elements. Each of the imaging elements is provided on a respective one of a plurality of jigs of the fixing device, and each imaging element has a pixel size that is at most 2.5 μm by 2.5 μm. The method also includes causing a test image to be projected onto the light separator, and receiving, by circuitry of the fixing device, signals generated by each of the imaging elements in response to the test image. The method further includes determining, by the circuitry of the fixing device, a registration error based on the signals generated by each of the imaging elements, and causing at least one jig to adjust a position of at least one of the imaging elements relative to the light separator in order to reduce the registration error to less than or equal to a threshold determined according to the pixel size.

In a further exemplary embodiment, a medical imaging system includes a medical imaging device that captures images of a subject, and circuitry that processes an image signal form the medical imaging device to display the images on a display. The medical imaging device includes a light separator that separates light into a plurality of light bands, and a plurality of imaging elements. Each imaging element receives one of the plurality of light bands and generates a corresponding signal. Each of the imaging elements has a pixel size of at most 2.5 μm by 2.5 μm. A registration error among the plurality of imaging elements being equal to or less than a threshold determined according to the pixel size.

Advantageous Effects of Invention

According to an embodiment of this technology, a light separation unit separates incident light into a plurality of wavelength regions. Imaging elements that generate imaging signals by performing photoelectric conversion using light with the wavelength regions obtained by the separation are provided for the respective wavelength regions obtained by the separation by the light separation unit. The imaging elements have a ⅔-inch size and 4K resolution. Registration errors of the imaging elements provided for the respective wavelength regions are limited to an error range of ±0.5 μm. Limiting registration errors in this manner enables an imaging device that can acquire captured images with high definition and high image quality to be provided easily and inexpensively. Note that the effects described in the present specification are merely illustrative, and not limitative; there may be additional effects.

BRIEF DESCRIPTION OF DRAWINGS

FIG. 1 illustrates an example of a configuration of an imaging device.

FIG. 2 illustrates the positional relation between a color separation prism and imaging elements.

FIG. 3 illustrates an example of a configuration of a fixing device.

FIG. 4 is a view for describing the relation between contrast and a registration error.

FIG. 5 illustrates the relation between registration errors and contrast in 4K resolution.

FIG. 6 illustrates the relation between pixel sizes and contrast for each aperture value when an ideal lens is used.

FIG. 7 illustrates the relation between registration errors and contrast in 4K resolution for each aperture value when an ideal lens is used.

FIG. 8 schematically illustrates a case where an imaging element for red has exhibited misalignment with respect to an imaging element for green in a rotation direction.

FIG. 9 is an explanatory view for describing an example of a schematic configuration of a surgery system in which an imaging device according to an embodiment of the present disclosure is applied to a medical observation device.

DESCRIPTION OF EMBODIMENTS

Hereinafter, modes for carrying out the present technology will be described. The description is given in the following order.

1. Configuration of imaging device
2. Configuration and operation of fixing device of imaging element
3. Application example 1. Configuration of Imaging Device Hereinafter, an embodiment of this technology will be described. In the embodiment, an example is shown in which incident light is separated into components of red, green, and blue, for example, and imaging signals corresponding to the respective color components are generated by imaging elements provided for the respective colors.

FIG. 1 illustrates an example of a configuration of an imaging device. An imaging device 10 includes a light separation unit that separates incident light into a plurality of wavelength regions, for example, a color separation prism 20 that separates object light incident via a lens into components of red, green, and blue. The imaging device 10 also includes imaging elements for the respective wavelength regions obtained by the separation by the light separation unit. The imaging elements generate imaging signals by performing photoelectric conversion using light with the wavelength regions obtained by the separation. For example, the imaging device 10 includes imaging elements 31R, 31G, and 31B.

The imaging elements 31R, 31G, and 31B are complementary metal oxide semiconductor (CMOS) imaging elements, charge coupled device (CCD) imaging elements, or the like. The imaging element 31R is fixed to a red-light-emitting surface of the color separation prism 20 via a fixing glass plate (fixing plate) 42R, being held by fixing glasses (fixing members) 41R. Similarly, the imaging element 31G (31B) is fixed to a green-light-(blue-light-)emitting surface of the color separation prism 20 via a fixing glass plate (fixing plate) 42G (42B), being held by fixing glasses (fixing members) 41G (41B). The imaging element 31R is mounted on a substrate 32R, and the imaging element 31G (31B) is mounted on a substrate 32G (32B).

The imaging element 31R performs photoelectric conversion using light with the red wavelength region obtained by the separation by the color separation prism 20 to generate imaging signals. Similarly, the imaging element 31G performs photoelectric conversion using light with the green wavelength region obtained by the separation by the color separation prism 20 to generate imaging signals, and the imaging element 31B performs photoelectric conversion using light with the blue wavelength region obtained by the separation by the color separation prism 20 to generate imaging signals.

FIG. 2 illustrates the positional relation between a color separation prism and imaging elements. Note that fixing glasses, fixing glass plates, and substrates are omitted from FIG. 2 for easy understanding.

Object light enters a light incident surface 21 of the color separation prism 20. A green component of the object light is separated by a block 22G of the color separation prism 20, and an image of light of the green component is formed on a light-receiving surface of the imaging element 31G. Next, a blue component of light that has passed through the block 22G of the color separation prism 20 is separated by a block 22B of the color separation prism 20, and an image of light of the blue component is formed on a light-receiving surface of the imaging element 31B. Then, an image of light that has passed through the blocks 22G and 22B of the color separation prism 20, that is, light of a red component, is formed on a light-receiving surface of the imaging element 31R through a block 22R.

In the imaging device 10 with such a configuration, the imaging elements 31R, 31G, and 31B are positioned with respect to the color separation prism 20, and then fixed to the color separation prism 20 with an adhesive. As the adhesive, a UV curable adhesive or the like that has low cure shrinkage and is cured in a short time is used in order to increase the accuracy of fixing between components.

2. Configuration and Operation of Fixing Device

FIG. 3 illustrates an example of a configuration of a fixing device that fixes imaging elements to a color separation prism. A fixing device 50 includes a light source unit 51 and position adjustment jigs 52R, 52G, and 52B, element driving units 53R, 53G, and 53B, and amplifiers 54R, 54G, and 54B for the respective colors. The fixing device 50 also includes a memory unit 55, a timing generator 56, a signal processing unit 57, a display unit 58, and a measurement unit 59.

The light source unit 51 causes object light of a test image or the like that is used in fixing the imaging elements 31R, 31G, and 31B to enter the color separation prism 20.

The position adjustment jig 52R for red is a mechanism for adjusting the position of the imaging element 31R for red with respect to the color separation prism 20. The position adjustment jig 52G for green is a mechanism for adjusting the position of the imaging element 31G for green with respect to the color separation prism 20. The position adjustment jig 52B for blue is a mechanism for adjusting the position of the imaging element 31B for blue with respect to the color separation prism 20.

The element driving unit 53R for red drives the imaging element 31R for red, causing the imaging element 31R to generate a red component imaging signal based on light of the red component separated from the object light that has entered the color separation prism 20. The element driving unit 53G for green drives the imaging element 31G for green, causing the imaging element 31G to generate a green component imaging signal based on light of the green component separated from the object light that has entered the color separation prism 20. The element driving unit 53B for blue drives the imaging element 31B for blue, causing the imaging element 31B to generate a blue component imaging signal based on light of the blue component separated from the object light that has entered the color separation prism 20.

The amplifier 54R for red amplifies the red component imaging signal generated by the imaging element 31R with a predetermined gain and outputs the resulting imaging signal to the memory unit 55. The amplifier 54G for green amplifies the green component imaging signal generated by the imaging element 31G with a predetermined gain and outputs the resulting imaging signal to the memory unit 55. The amplifier 54B for blue amplifies the blue component imaging signal generated by the imaging element 31B with a predetermined gain and outputs the resulting imaging signal to the memory unit 55.

The memory unit 55 stores the imaging signals supplied from the imaging elements 31R, 31G, and 31B, reads the stored imaging signals at a predetermined speed, and outputs the read imaging signals to the signal processing unit 57.

The timing generator 56 generates timing signals and supplies the timing signals to the element driving units 53R, 53G, and 53B and the memory unit 55 to make it possible to synchronously perform the generation of imaging signals in the imaging elements 31R, 31G, and 31B and the storage of imaging signals in the memory unit 55. The timing generator 56 supplies the timing signals to the memory unit 55, thereby allowing the stored imaging signals to be read at a predetermined speed and output to the signal processing unit 57.

The signal processing unit 57 converts the imaging signals read from the memory unit 55 to image signals compatible with the display unit 58 and the measurement unit 59, and outputs the image signals after the conversion to the display unit 58 and the measurement unit 59. In addition, the signal processing unit 57 may supply RAW signals of the imaging elements, for example, to the measurement unit 59 so that the measurement unit 59 can detect registration errors accurately.

The display unit 58 displays a test image or the like based on the image signals supplied from the signal processing unit 57. The measurement unit 59 measures registration errors of the imaging elements 31R, 31G, and 31B, based on the image signals supplied from the signal processing unit 57.

Next, the relation between the contrast of a luminance signal and a registration error is described. The luminance signal is based on ITU-R Recommendation BT2020-1, which defines an ultra-high definition video format, such as 4K resolution. A luminance signal Y is calculated from a red component imaging signal R, a green component imaging signal G, and a blue component imaging signal B, as expressed by Formula (1). A contrast Dct is calculated based on Formula (2).

$$Y = 0.2627R + 0.6780G + 0.0593B \tag{1}$$

$$Dct = (Y\max - Y\min)/(Y\max + Y\min) \tag{2}$$

FIG. 4 is a view for describing the relation between contrast and a registration error. FIG. 4 illustrates an example in which a registration error has occurred in the horizontal direction.

In FIG. 4, (A) illustrates a test image that enters the color separation prism 20. The test image is a binary image of white and black in which a white region (corresponding to one pixel or a plurality of pixels) and a black region (corresponding to one pixel or a plurality of pixels) are provided alternately in the horizontal direction.

In FIG. 4, (B) illustrates a state where the positions of pixels of individual colors coincide with each other in the horizontal direction as well. Note that in (B) and (E) of FIG. 4, pixels of individual colors whose positions in the vertical direction coincide with each other are arranged in the vertical direction so that the positional relation between the pixels of the individual colors in the horizontal direction can be understood easily.

In FIG. 4, (C) illustrates an image based on luminance signals in a state where the positions of the pixels of the individual colors coincide with each other. In the state where the positions of the pixels of the individual colors coincide with each other, since the test image is a binary image of white and black, the image based on the luminance signals is equal to the test image. In FIG. 4, (D) illustrates the relation between pixel positions and luminance signals in this state. The contrast Dct of the image is high.

In FIG. 4, (E) illustrates an example in which red and blue pixels exhibit registration errors with respect to green pixels in the horizontal direction. In this case, since the red and blue pixels are misaligned with the green pixels, white pixels of the test image exhibit a chromatic color instead of white, and black pixels of the test image exhibit a chromatic color instead of black, as illustrated in (F) of FIG. 4. Accordingly, an image based on luminance signals is different from the test image, and the relation between pixel positions and luminance signals is as illustrated in (G) of FIG. 4. That is, the contrast Dct is lowered as compared with the case where the positions of the pixels of the individual colors coincide with each other.

In the imaging device 10, the resolution of the imaging elements 31R, 31G, and 31B is set to 4K so that high-definition captured images can be provided. In addition, the size of the imaging elements 31R, 31G, and 31B is set to a ⅔-inch size, which is equal to the size of imaging elements in related art, so that lenses that have been numerously provided can be applied. When such imaging elements adopt 4K resolution (3840 pixels×2160 pixels), the pixel size is "2.5 μm×2.5 μm". Note that 4K resolution also includes "4096 pixels×2160 pixels", in which case the pixels size is smaller than "2.5 μm×2.5 μm". Of course, other, higher, resolutions are possible, such as 8K. Therefore, the pixels of the imaging elements 31R, 31G and 31B are at most 2.5 μm×2.5 μm, but may be smaller for higher resolutions.

FIG. 5 illustrates the relation between registration errors and contrast in 4K resolution. Note that FIG. 5 assumes a case where red and blue pixels exhibit the same amount of misalignment in the same direction with respect to green pixels and the pixel size is "2.5 μm×2.5 μm". In addition, the contrast when the registration error is "0" is assumed to be 100 percent. Here, when the lower limit of contrast degradation is set to approximately 90 percent, the registration errors fall within a range of "±0.5 μm".

When an ideal lens without aberration is used, the contrast changes as illustrated in FIG. 6 in accordance with pixel sizes and aperture values. FIG. 6 illustrates the relation between pixel sizes and contrast for each aperture value when an ideal lens and an e-line (546 nm) are used. In FIG. 6, the contrast when the registration error is "0" in a state without an ideal lens is assumed to be 100 percent. Here, in the case where the aperture value is "f/4.0", which is used often in capturing moving images, the contrast is 70 percent or more when the pixel size is "5 μm×5 μm", and the contrast is 50 percent or less when the pixel size is "2.5 μm×2.5 μm".

FIG. 7 illustrates the relation between registration errors and contrast in 4K resolution for each aperture value when an ideal lens is used. The imaging device limits registration errors so that the contrast satisfies a desired level or more for an aperture value that is used frequently in capturing moving images. Here, since the aperture value is often set to "f/4.0", an error range of registration errors is set such that the contrast becomes 40 percent, which is a desired level, or more when the aperture value is "f/4.0", for example. That is, the imaging device limits registration errors to an error range of ±0.5 μm. Here, when 4K resolution is "3840 pixels×2160 pixels", the error range of ±0.5 μm corresponds to a range of 20 percent or less of the pixel size in an imaging element. Accordingly, the imaging device limits registration errors to a range of 20 percent or less of the pixel size, for example, which is within an error range of ±0.5 μm. Note that the desired level of contrast assuming an ideal lens corresponds to a level that is allowable even if contrast is lowered by registration errors when imaging is actually performed.

Registration errors may occur not only in the horizontal direction or the vertical direction but also in a rotation direction around an optical axis direction as a rotation axis. Accordingly, rotation is limited so that registration errors fall within a range of 20 percent or less of the pixel size, for example, which is within an error range of ±0.5 μm, even if a shift in the rotation direction occurs.

FIG. 8 schematically illustrates a case where the imaging element for red has exhibited misalignment with respect to the imaging element for green in the rotation direction.

As illustrated in (A) of FIG. 8, when the imaging element rotates in the direction of an arrow FR with a center position CP serving as an axis, the amount of movement of the outermost pixel Pa, which is farthest from the center, becomes the largest. Accordingly, as illustrated in (B) of FIG. 8, misalignment in the rotation direction is limited so that the amounts of movement dH and dV of the outermost pixel Pa both fall within a range of 20 percent or less of the pixel size, for example, which is within an error range of ±0.5 μm.

Here, when the imaging element has a ⅔-inch size and a diagonal length of 11 mm, the outermost pixel Pa is 5.5 mm away from the center. In addition, when the imaging element has a ⅔-inch size and 4K resolution (3840 pixels×2160 pixels), registration errors are limited to an error range of ±0.5 μm. Accordingly, a shift in the rotation direction is limited so that a rotation angle θ is equal to or smaller than a rotation angle at which the amounts of movement dH and dV both become 0.5 μm. Here, the rotation angle θ at which the amount of movement dH becomes 0.5 μm is 0.011 degrees, and the rotation angle θ at which the amount of movement dV becomes 0.5 μm is 0.006 degrees. Accordingly, when there is no error of the center position of the imaging element, misalignment in the rotation direction is limited to a range of "±0.006 degrees".

The fixing device 50 limits registration errors of the imaging elements provided for the respective wavelength regions to a range of 20 percent or less of the pixel size, for example, which is within an error range of ±0.5 μm.

The fixing device 50 fixes the imaging element 31G for green, for example, to the color separation prism 20. Then, the fixing device 50 adjusts the positions of the imaging element 31R for red and the imaging element 31B for blue, using the imaging element 31G for green as a reference. Specifically, the fixing device 50 adjusts the position of the imaging element 31R for red (the imaging element 31B for blue) so that a registration error of the imaging element 31R for red (the imaging element 31B for blue) with respect to the imaging element 31G for green is limited to a range of 20 percent or less of the pixel size, for example, which is within an error range of ±0.5 μm. The fixing device 50 fixes the imaging element 31R for red and the imaging element 31B for blue whose positions have been adjusted to the color separation prism 20.

Thus, according to an embodiment of this technology, when imaging elements having 4K resolution and a ⅔-inch size, which allows application of lenses that have been provided, are used, registration errors are limited to a range of 20 percent or less of the pixel size, for example, which is within an error range of ±0.5 μm. Accordingly, the imaging elements are fixed to the color separation prism such that adverse effects of registration errors fall within an allowable range; thus, the imaging device can be provided more easily and inexpensively as compared with a case where an imaging device is manufactured to be free from registration errors.

As a method for compensating registration errors, a method of performing electrical compensation on imaging signals generated by imaging elements has been proposed. However, this method requires a signal processing circuit for the compensation, and may not be able to perform compensation depending on shift directions. In contrast, in an embodiment of this technology, the imaging elements are fixed to the color separation prism such that registration errors are limited to a range of 20 percent or less of the pixel size, for example, which is within an error range of ±0.5 μm; thus, it is possible to control adverse effects of registration errors to within an allowable range, regardless of shift directions. Accordingly, the imaging device 10 can generate captured images with high definition and high image quality. Note that when 4K resolution is "4096 pixels×2160 pixels", the pixel size is smaller than that for "3840 pixels×2160 pixels". Accordingly, by limiting registration errors to a range of 20 percent or less of the pixel size, for example, which is within an error range of ±0.5 μm, it is possible to control adverse effects of registration errors to within an allowable range even with a resolution of "4096 pixels×2160 pixels".

3. Application Example

An example of a configuration of a surgery system in which an imaging device according to the present embodiment is applied to a medical observation device is described with reference to FIG. 9. FIG. 9 is an explanatory view for describing an example of a schematic configuration of a surgery system in which an imaging device according to the present embodiment is applied to a medical observation device.

For example, FIG. 9 illustrates an example of an endoscopic surgery system 100 in which an imaging device according to the present embodiment is used as a rigid endoscope used in endoscopic surgery for the abdomen, which is performed in medical sites in place of abdominal surgery in related art. As illustrated in FIG. 9, in endoscopic surgery for the abdomen, instead of cutting the abdominal wall for laparotomy as in related art, hole-making tools called trocars 250a and 250b are attached to a few spots of the abdominal wall, and a laparoscope (hereinafter also called endoscope) 110, an energy treatment tool 220, forceps 230, and the like are inserted into the body through holes of the trocars 250a and 250b. Then, while images of the affected part (a tumor or the like) U obtained by video imaging by using the endoscope 110 are viewed in real time, treatment such as resecting the affected part U is performed by using the energy treatment tool 220 or the like. Note that the endoscope 110, the energy treatment tool 220, and the forceps 230 are held by an operator, an assistant, a scopist, a robot, or the like.

In a surgical room where such endoscopic surgery is performed, a cart 310 that carries devices for the endoscopic surgery, a patient bed 330 where the patient lies, a foot switch 350, and the like are arranged. The cart 310 is equipped with, for example, devices such as a camera control unit (CCU) 130, a light source device 170, a device 210 for a treatment tool, a pneumoperitoneum device 240, a display device 150, a recorder 260, and a printer 270, as medical equipment.

The endoscope 110 generates image signals of the affected part U by imaging elements provided for the respective wavelength regions, and transmits the image signals to the CCU 130 via a camera cable. Note that the CCU 130 may be connected to the endoscope 110 via a camera cable, or may be connected to the endoscope 110 via a wireless communication path. The CCU 130 performs signal processing on the image signals output from the endoscope 110, and outputs the image signals after the signal processing to the display device 150. Such a configuration allows an endoscopic image of the affected part U to be displayed on the display device 150.

The CCU 130 may output the image signals after the signal processing to the recorder 260 to record the endoscopic image of the affected part U as image data (e.g., data of a moving image) in the recorder 260. Furthermore, the CCU 130 may output the image signals after the signal processing to the printer 270 to cause the printer 270 to print the endoscopic image of the affected part U.

The light source device 170 is connected to the endoscope 110 via a light guide cable and is able to illuminate the affected part U, switching between light with various wavelengths. Note that light emitted from the light source device 170 is used as auxiliary light, for example, in some cases.

The device 210 for a treatment tool corresponds to, for example, a high-frequency output device that outputs high-frequency current to the energy treatment tool 220 that cuts the affected part U using electrical heat.

The pneumoperitoneum device 240 includes an air supplying and sucking mechanism and supplies air to the abdominal region, for example, inside the patient's body.

The foot switch 350 controls the CCU 130, the device 210 for a treatment tool, and the like using foot operation by the operator, the assistant, and the like as trigger signals.

An example of a schematic system configuration of the endoscopic surgery system 100 has been described above, with reference to FIG. 9, as a system configuration in which an imaging device according to an embodiment of the present disclosure is applied to a rigid endoscope; however, an imaging device according to an embodiment of the present disclosure can also be applied to a medical observation device such as a surgical microscope.

Note that the effects described in the present specification are merely illustrative, and not limitative; there may be additional effects that are not described. In addition, it should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An imaging device, comprising: a light separator configured to separate light into a plurality of light bands; and a plurality of imaging elements, each configured to receive one of the plurality of light bands and to generate a corresponding signal, each of the imaging elements having a pixel size of at most 2.5 µm by 2.5 µm, wherein a registration error among the plurality of imaging elements is equal to or less than a threshold determined according to the pixel size.

(2) The imaging device of (1), wherein the threshold is substantially 20% of the pixel size.

(3) The imaging device of (2), wherein the threshold is 5 µm.

(4) The imaging device of any one of (1) to (3), wherein the light separator is a prism.

(5) The imaging device of any one of (1) to (4), wherein the light bands include a red light band, a green light band and a blue light band.

(6) The imaging device of any one of (1) to (5), wherein the imaging elements are of ⅔-inch size and have substantially 4K resolution.

(7) The imaging device of (6), wherein the imaging elements include at least 3840 horizontal pixels.

(8) The imaging device of any one of (1) to (7), wherein the registration error is determined based on contrast degradation.

(9) The imaging device of (8), wherein the contrast degradation is determined by the circuitry of the fixing device at a predetermined f-stop.

(10) The imaging device of (9), wherein the predetermined f-stop is f/4.0.

(11) A method of manufacturing an imaging device, the method comprising: providing a light separator on a fixing device; providing a plurality of imaging elements, each on a respective one of a plurality of jigs of the fixing device, each imaging element having a pixel size that is at most 2.5 µm by 2.5 µm; causing a test image to be projected onto the light separator; receiving, by circuitry of the fixing device, signals generated by each of the imaging elements in response to the test image; determining, by the circuitry of the fixing device, a registration error based on the signals generated by each of the imaging elements; and causing at least one jig to adjust a position of at least one of the imaging elements relative to the light separator in order to reduce the registration error to less than or equal to a threshold determined according to the pixel size.

(12) The method of manufacturing an imaging device of (11), further comprising fixing each of the imaging elements to the light separator using an adhesive.

(13) The method of manufacturing an imaging device of (12), wherein the adhesive is an ultra-violet (UV) curable adhesive.

(14) The method of manufacturing an imaging device of any one of (11) to (13), wherein the registration error is determined based on contrast degradation.

(15) The method of manufacturing an imaging device of (14), wherein the contrast degradation is determined by the circuitry of the fixing device at a predetermined f-stop.

(16) The method of manufacturing an imaging device of (15), wherein the predetermined f-stop is f/4.0.

(17) The method of manufacturing an imaging device of any one of (11) to (16), wherein the threshold is substantially 20% of the pixel size.

(18) The method of manufacturing an imaging device of any one of (11) to (17), wherein the threshold is a registration error of 5 µm.

(19) The method of manufacturing an imaging device of any one of (11) to (18), wherein the light separator is a prism.

(20) The method of manufacturing an imaging device of any one of (11) to (19), where in the plurality of imaging elements include an imaging element configured to capture red light, an imaging element configured to capture green light and an imaging sensor configured to capture blue light.

(21) A medical imaging system, comprising: a medical imaging device configured to capture images of a subject; and circuitry configured to process an image signal form the medical imaging device to display the images on a display, wherein the medical imaging device includes: a light separator configured to separate light into a plurality of light bands; and a plurality of imaging elements, each configured to receive one of the plurality of light bands and to generate a corresponding signal, each of the imaging elements having a pixel size of at most 2.5 μm by 2.5 μm, wherein a registration error among the plurality of imaging elements being equal to or less than a threshold determined according to the pixel size.

(22) The medical imaging system of (21), wherein the medical imaging device is an endoscope.

(23) The medical imaging system of (21) or (22), wherein the imaging elements have at least substantially 4K resolution.

(24) The medical imaging system of any one of (21) to (23), wherein the threshold is substantially 20% of the pixel size.

(25) An imaging device including:
a light separation unit configured to separate incident light into a plurality of wavelength regions; and
imaging elements provided for the respective wavelength regions obtained by the separation by the light separation unit and configured to generate imaging signals by performing photoelectric conversion using light with the wavelength regions obtained by the separation,
wherein the imaging elements have a ⅔-inch size and 4K resolution, and registration errors of the imaging elements provided for the respective wavelength regions are limited to an error range of ±0.5 μm.

(26) The imaging device according to (25),
wherein the error range is a range of 20 percent or less of a pixel size in the imaging element.

(27) The imaging device according to (25) or (26),
wherein the error range is set based on a relation between a registration error and contrast when an ideal lens is used.

INDUSTRIAL APPLICABILITY

An imaging device that a light separator that separates light into a plurality of light bands, and a plurality of imaging elements that each receive one of the plurality of light bands and generates a corresponding signal, where each of the imaging elements has a pixel size of at most 2.5 μm by 2.5 μm, and a registration error among the plurality of imaging elements is equal to or less than a threshold determined according to the pixel size, reduces the distortion cause by registration errors which become more pronounced as pixel sizes decrease.

REFERENCE SIGNS LIST 10 imaging device
20 color separation prism
21 light incident surface
22R, 22G, 22B block
31R, 31G, 31B imaging element
32R, 32G, 32B substrate
50 fixing device
51 light source unit
52R, 52G, 52B position adjustment jig
53R, 53G, 53B element driving unit
54R, 54G, 54B amplifier
55 memory unit
56 timing generator
57 signal processing unit
58 display unit
59 measurement unit
100 endoscopic surgery system
110 endoscope
130 CCU
150 display device
170 light source device
210 device for treatment tool
220 energy treatment tool
230 forceps
240 pneumoperitoneum device
250a, 250b trocar
260 recorder
270 printer
310 cart
330 patient bed
350 foot switch

The invention claimed is:

1. An imaging device, comprising:
a light separator configured to separate light into a plurality of light bands; and
a plurality of imaging elements, each of the plurality of imaging elements configured to receive one of the plurality of light bands and to generate a corresponding signal, each of the plurality of imaging elements having a pixel size of at most 2.5 μm by 2.5 μm,
wherein a registration error among the plurality of imaging elements is equal to or less than a threshold of 0.5 μm.

2. The imaging device according to claim 1, wherein the light separator is a prism.

3. The imaging device according to claim 1, wherein the plurality of light bands include a red light band, a green light band, and a blue light band.

4. The imaging device according to claim 1, wherein each of the plurality of imaging elements is of ⅔-inch size and has 4K resolution.

5. The imaging device according to claim 4, wherein the plurality of imaging elements include at least 3840 horizontal pixels.

6. The imaging device according to claim 1, wherein the registration error is determined based on contrast degradation.

7. The imaging device according to claim 6, wherein the contrast degradation is determined by circuitry of a fixing device at a predetermined f-stop.

8. The imaging device according to claim 7, wherein the predetermined f-stop is f/4.0.

9. A medical imaging system, comprising:
a medical imaging device configured to capture images of a subject; and
circuitry configured to process an image signal from the medical imaging device to display the images on a display,
wherein the medical imaging device includes:
a light separator configured to separate light into a plurality of light bands; and
a plurality of imaging elements, each of the plurality of imaging elements configured to receive one of the plurality of light bands and to generate a corresponding signal, each of the plurality of imaging elements having a pixel size of at most 2.5 μm by 2.5 μm, a registration error among the plurality of imaging elements being equal to or less than a threshold of 0.5 μm.

10. The medical imaging system according to claim 9, wherein the medical imaging device is an endoscope.

11. The medical imaging system according to claim 9, wherein the plurality of imaging elements have at least 4K resolution.

12. The medical imaging system according to claim 9, wherein the light separator is a prism, and the plurality of imaging elements include an imaging element configured to capture red light, an imaging element configured to capture green light, and an imaging capture element configured to capture blue light.

* * * * *